United States Patent [19]

Johnston

[11] 4,349,195

[45] Sep. 14, 1982

[54] STANDING SUPPORT FOR HANDICAPPED PERSONS

[76] Inventor: Malcolm Johnston, 46 Ladbroke Sq., London, England, W11 3ND

[21] Appl. No.: 149,612

[22] Filed: May 14, 1980

[30] Foreign Application Priority Data

May 15, 1979 [GB] United Kingdom ................. 7916851

[51] Int. Cl.³ .......................... A63B 21/00; A61F 3/00

[52] U.S. Cl. ................................ 272/134; 128/80 G; 272/138; 272/141; 272/144

[58] Field of Search ..................... 272/70.3, 70.4, 134, 272/135, 136, 137, 138, 139, 140, 141, 142, 93, 50, 36, 44; 128/68, 80 R, 80 G

[56] References Cited

U.S. PATENT DOCUMENTS 2,862,710 12/1958 Lewis ............................ 272/134 X
4,029,089 6/1977 Mulholland .................. 128/80 G X

*Primary Examiner*—Richard J. Apley
*Assistant Examiner*—Arnold W. Kramer
*Attorney, Agent, or Firm*—James C. Wray

[57] ABSTRACT

A standing support frame for handicapped persons comprising a platform (10), a column (17) mounted upright on the platform so as to be pivotable to a limited degree in all directions from a mean position, a pair of upright horizontally spaced support arms (40), the arms being joined at their lower ends to the column (17) and at their upper ends to a chest support (70), a knee support (30) mounted to the column, and a buttock support (60) extending between the arms at an appropriate position, means (M) being provided for resiliently urging the column to the mean position.

11 Claims, 20 Drawing Figures

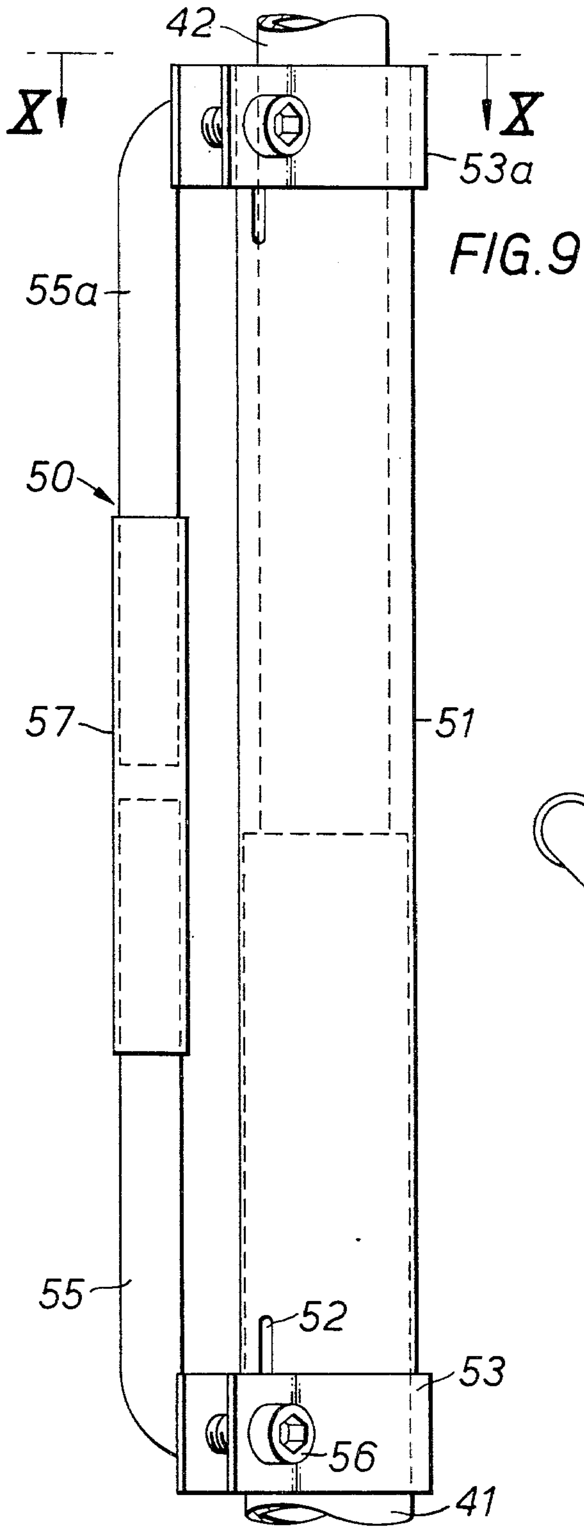
FIG. 9.
FIG. 10.
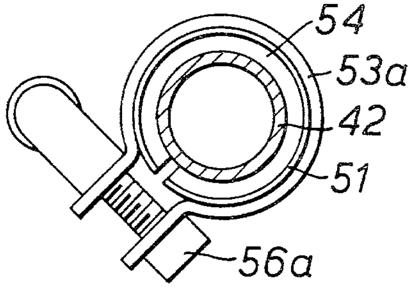

STANDING SUPPORT FOR HANDICAPPED PERSONS

The present invention relates to a support in the form of a standing frame for handicapped persons.

Hitherto very little has been done to assist patients who have difficulty in standing, although from a medical and a social point of view, it is undesirable for handicapped persons to spend the whole of their time in a seated position e.g. in a wheelchair. In many instances patients who cannot walk can be assisted to remain in a standing position, thereby utilising muscles they would otherwise be unable to use and prevent the formation of sores. It has also been found that it can be very encouraging to the morale of such patients to take part in activities of a social nature in a standing position.

Standing frames have been used for children of a simple kind comprising a base platform and a pair of vertical arms extending from the platform to which they are mounted on still rubber blocks to allow certain freedom of movement. The standing arms are joined in the buttock region by a canvas support and in the thorax region by a second canvas support. The arms thus extend behind the shoulders and can be gripped by the patient who is firmly held in a standing position with his feet on the platform. A padded bar is provided for supporting the knees.

These elementary devices have been found to be subject to disadvantages, notably the discomfort caused by the supports which are in no sense shaped to conform to the patient and by the fact that a pivoting movement of the arms is accompanied by a sliding vertical movement relative to the patient which is undesirable.

The present invention is aimed at overcoming or reducing these disadvantages.

One form of supporting frame in accordance with the invention comprises a platform, a column mounted upright on the platform so as to be pivotable to a limited degree in all directions from a mean position, a pair of upright horizontally spaced supporting arms, the arms being joined at their lower ends to the column and at their upper ends to a chest support, a knee support mounted to the column, and a buttock support extending between the arms at an appropriate position, means being provided for resiliently urging the column to the mean position.

The mounting of the upright arms to a single pivotable column allows the frame constituted by the arms and the various body supports to pivot as a whole with the body of the patient.

The knee support is preferably forward of the column, the arms extending rearwardly from the knee support, upwardly at a rearward spacing from the column and forwardly above the buttock support beyond the column axis to the chest support, the knee support including a cross-piece to which the arms are secured, the arms extending therefrom downwardly and then upwardly, an upper part of the column extending forwardly to join the knee support.

Preferably the knee support provides limited pivotal adjustment of the arms about a vertical axes. Means are preferably provided for maintaining the planar disposition of the arms during pivotal adjustment of the knee support.

In order to accommodate patients of different sizes who may often be partly deformed, numerous adjustments can preferably be made to various parts of the frame. Thus a telescopic section is preferably included in each arm so that the overall height of the frame can be adjusted. The height of the column itself can be adjusted also in the preferred case and the connection between the arms and the chest support is preferably slidably adjustable in a lateral direction, so that the spacing between the arms can be adjusted. The vertical angle of the chest support is preferably adjustable. The forward and rearward attitude of the upper part of the frame with respect to the column can preferably be adjusted by a rotatable mounting of the cross-piece to the column.

The platform is preferably mounted on castors with provision for locking the castors against movement e.g. by raising and lowering supports around the castors, relatively to the castors and the remainder of the platform.

Means are preferably provided for adjusting the degree of resiliency in the mounting of the column to the platform. In the preferred case the resilient means include respective lateral and front/rear articulations each converting pivotal movement of the column to horizontal piston movements, the piston movements being restrained by an adjustable resilient restraint which may be provided by a series of compressible blocks of elastomeric material such as rubber.

To allow sufficient comfort at the knee region, the knee support may include a pair of knee rests, each comprising a flexible preferably stretchable, tube e.g. of rubber which may be shaped by attachment to a shaped former such as a strip of metal. Preferably the tubes are filled with a fluid or gel which can be slightly displaced by the pressure of the knee. Some limited rotary movement of the tube section can also be provided.

An embodiment for the invention is hereafter described with reference to the accompanying drawings in which:

FIG. 9 is a partial side elevational view, enlarged, of one of the arms;

FIG. 10 is a section along X—X of FIG. 9;

Figure 1:
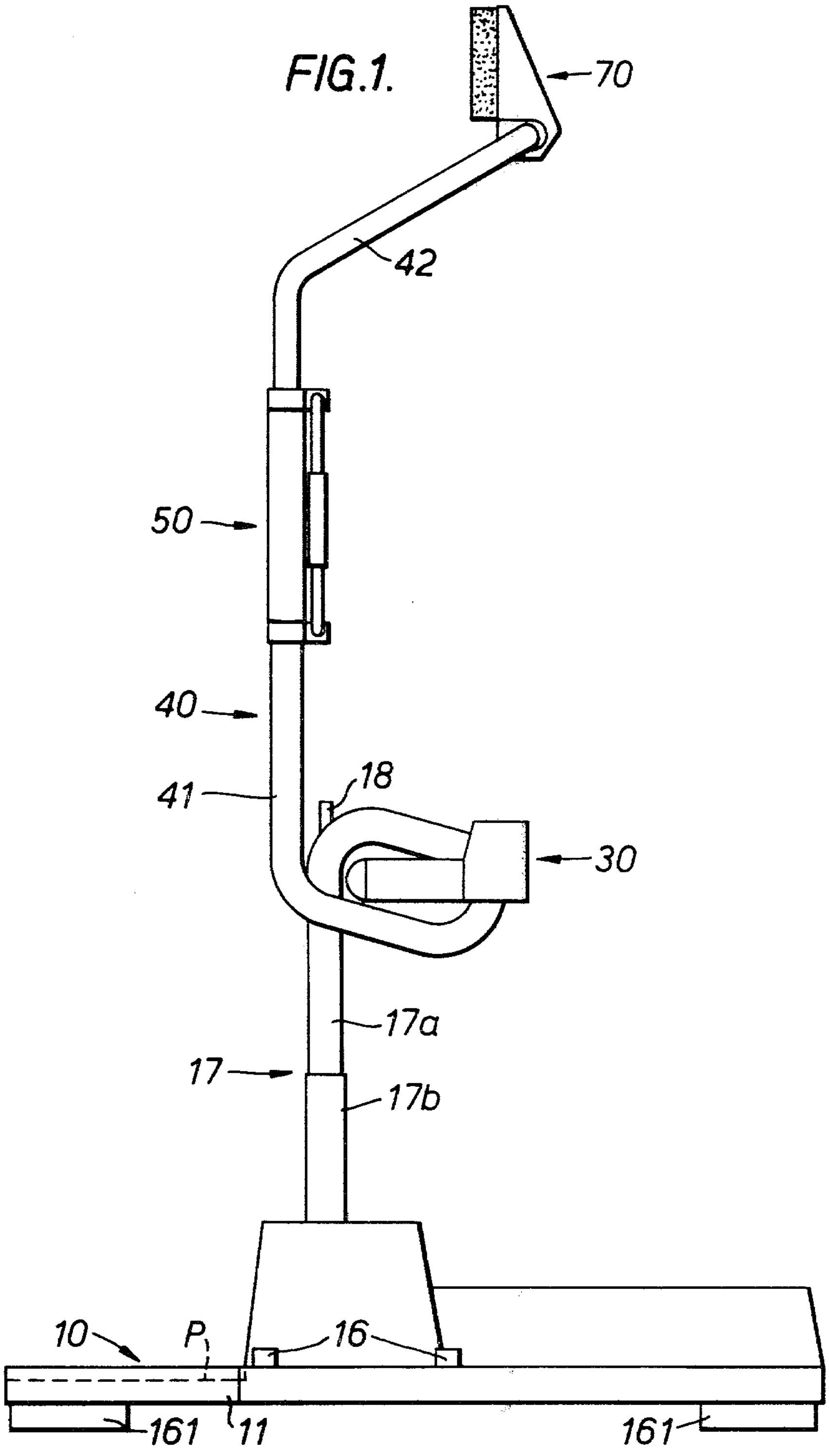
FIG. 1 shows a frame in accordance with the invention in side elevation.

The standing frame shown in the drawings with particular reference firstly to FIGS. 1 to 4 comprises a platform 10 having a floor section 11 and metal castor-mounting frames 12 to which are mounted castors 160. Rings 161 (or other supports) can be raised or lowered relatively to the floor section 11 around the castors 160 by means of a pedal P in any known or convenient manner. A preferred means will be described hereafter. The rings 161 rest on the floor in the position shown in the drawings to maintain the platform 10 stationary when the castors and platform are raised relatively thereto.

The upper surface of the platform 10 is provided with a metal grid 15 which provides locations for feet positioning studs 16.

Figure 2:
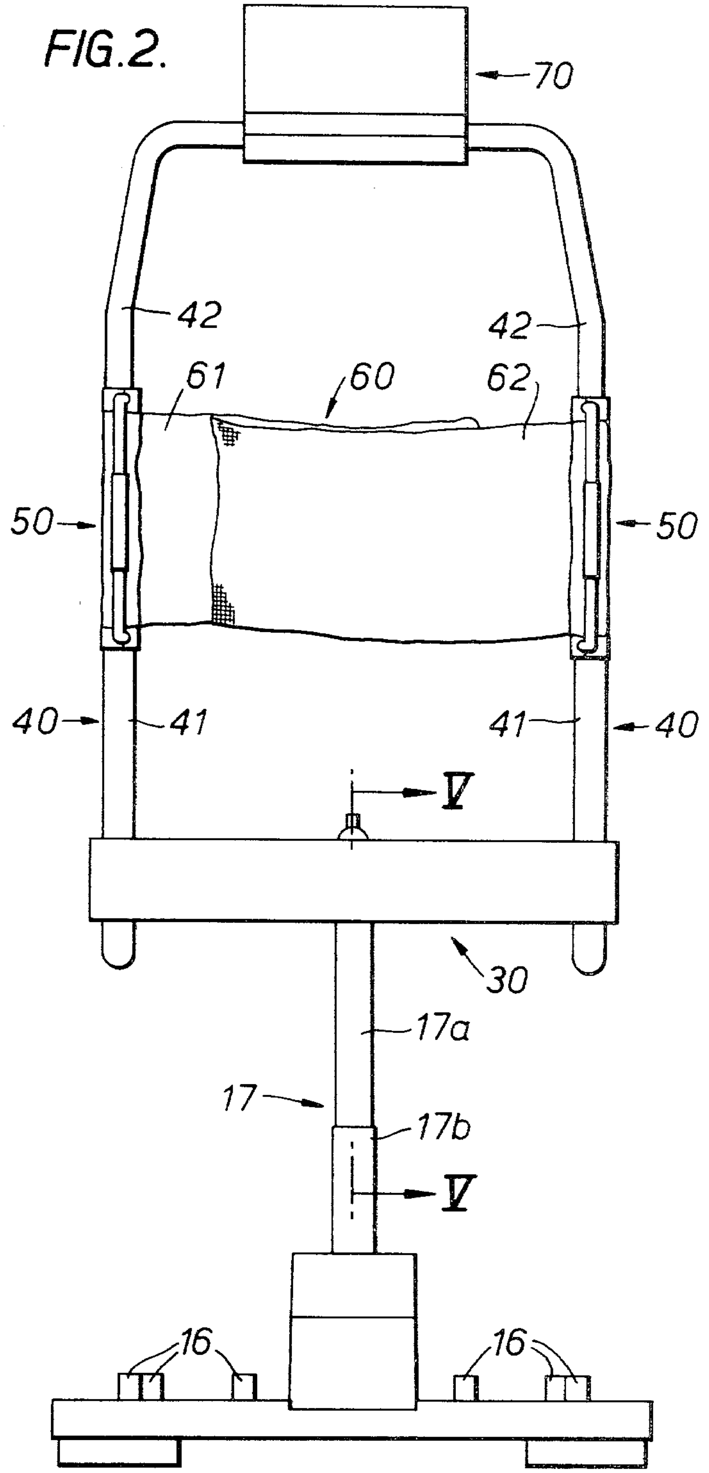
FIG. 2 shows the frame of FIG. 1 viewed from the front.

A central column 17 having telescopic section ***17a*, *17b* is pivotably mounted to the platform 10 at a position centrally between the patient's foot positions, so that its upper end can be moved against a biasing means in any direction from the upright means position shown in FIGS. 1 and 2**. This can be accomplished in any known manner e.g. by connecting the foot of the column to the platform through a rubber block or equivalent element. However a preferred means will be described hereafter, which incorporates a means for adjusting the resiliency of the coupling.

Figure 5:
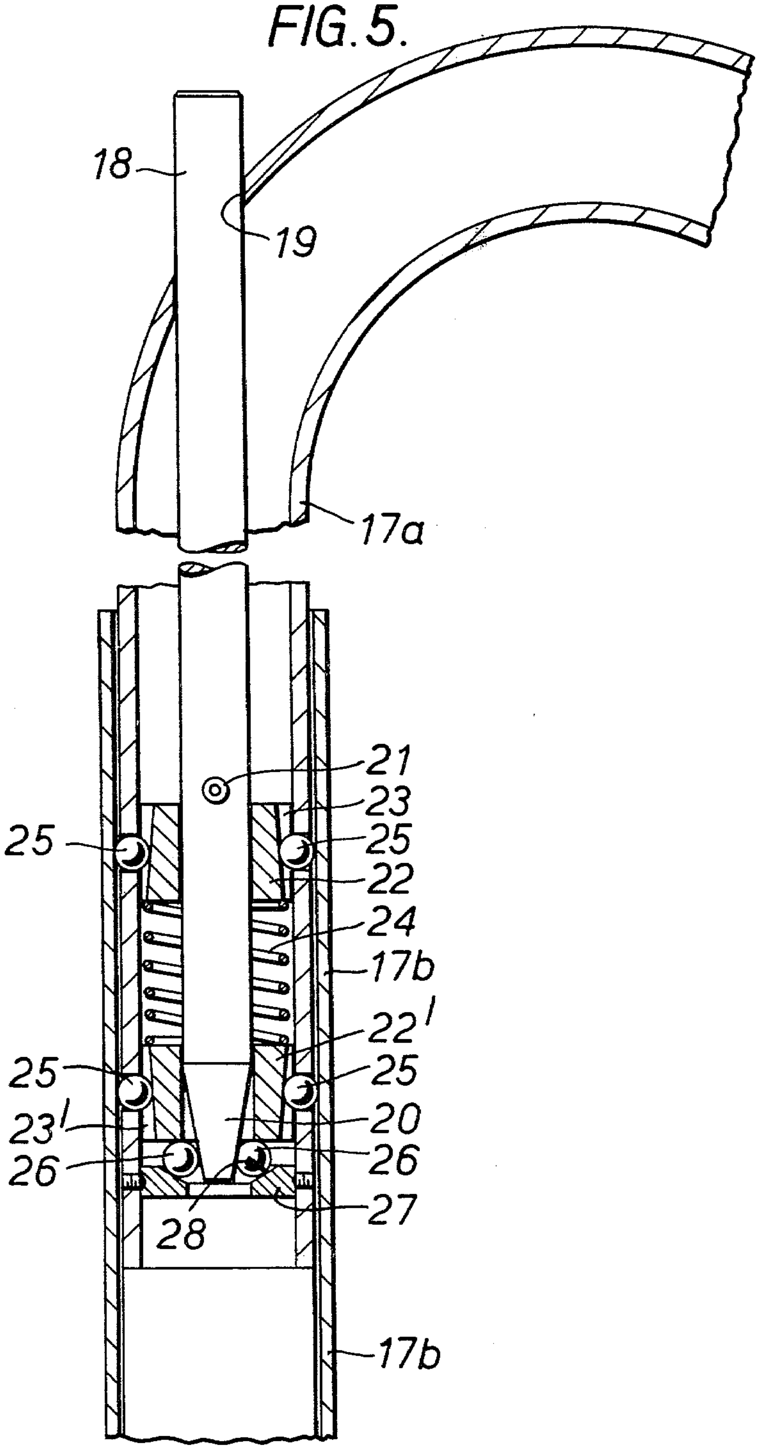
FIG. 5 is a section along the line V—V of FIG. 2 showing the column height adjustment.

The telescopic joint between sections ***17a*,*17b* of the column is shown in more detail in FIG. 5. A rod 18 passes through an aperture 19 in the curved portion of the upper column part *17a* and passes centrally through the lower part of *17a*, terminating in a tapered end portion 20. A pin 21 extends diametrically through the rod 18 at a distance from its lower end. The pin 21 bears against a ring 22 which has four tapered slots 23 equally spaced around its circumference. A similar ring 22' is vertically spaced from the ring 22 by a compression spring 24 and has corresponding slots 23'. The slots 23 taper radially in a downward direction and the slots 23' taper radially in an upward direction. Resting in the appropriate slots, in apertures in the column section *17a* are balls 25**.

The tapered end portion 20 of rod 18 bears against circumferentially arranged balls 26 which rest upon a plug 27 secured across the column section *17a*, the plug 27 being formed with a conical sloping shoulder 28.

When downward pressure is applied to the rod 18, the pin 21 bears against the ring 22 which is pressed downwardly against the compression spring 24. Simultaneously the tapered end portion 20 of the rod 18 presses apart the balls 26 which ride up the conical shoulder 28 of the plug and lift the ring 22', so that the two rings are pressed towards one another. This releases the balls 25 from their normal outward pressure against the column section *17b*, so that the two sections ***17a*,*17b* can be adjusted. As soon as pressure is released from the rod 18 the balls 25 are clamped in place between the rings and the interior surface of the column portion *17b*, so that the two column sections *17a*,*17b*** are clamped together.

Figure 6:
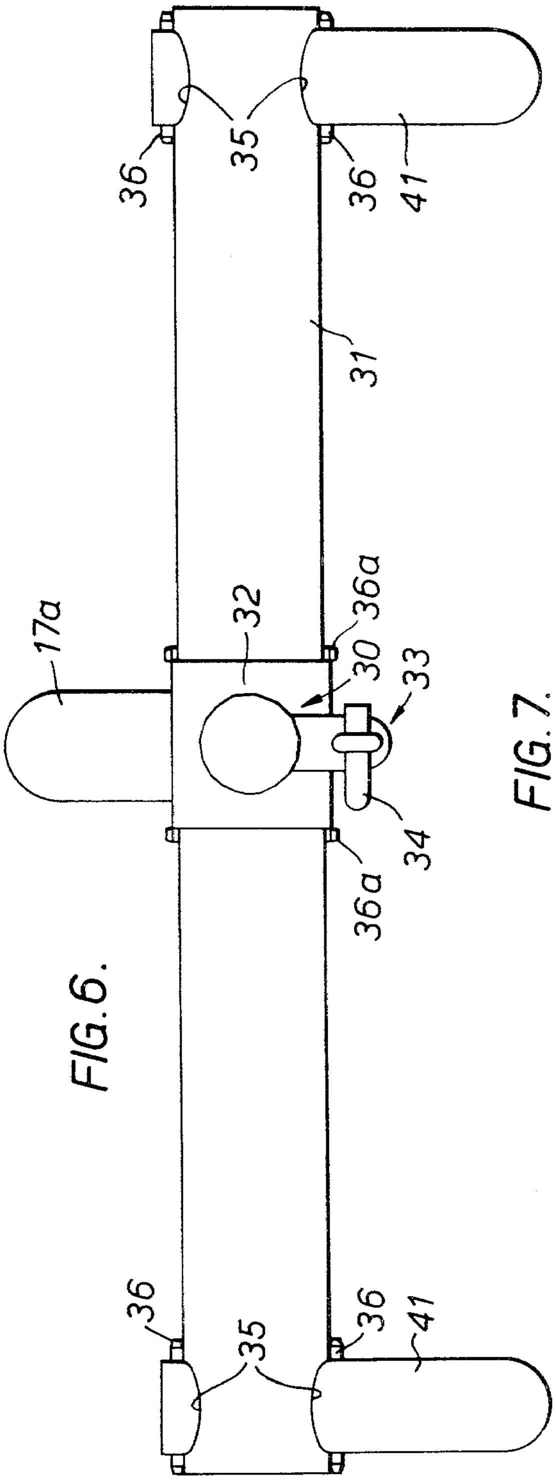
FIG. 6 is a front view of part of the knee support.
Figure 7:
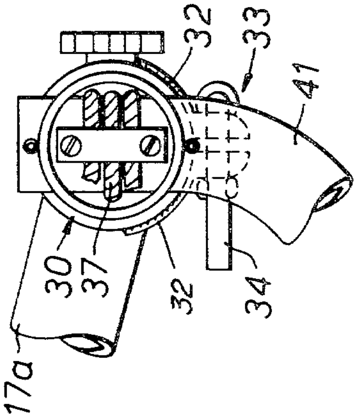
FIG. 7 is an end view of an elevation corresponding to FIG. 6.
Figure 8:
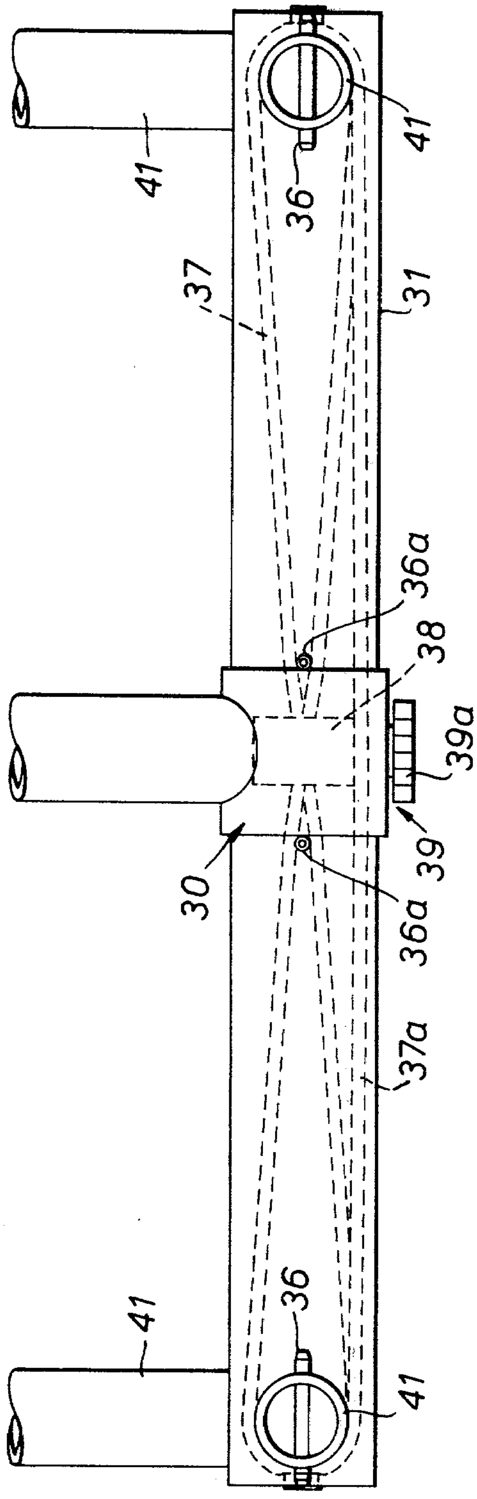
FIG. 8 is a plan view corresponding to FIG. 6.

The knee support assembly is shown in FIGS. 6, 7 and 8. The upper column section *17a* is welded to a split ring 30 through which passes a cross-piece in the form of a tube 31 so that the tube can be rotatably adjusted. Sections 32 of a proprietary clamp unit 33 are welded to respective split sections of the split tube 30, the clamp unit 33 including a lever 34 which operates by a camming action to clamp the sections 32 together to secure the tube 31 from rotation. It will be appreciated that the upper end portion of the column section *17a* is bent forwardly as viewed in FIG. 1 so that the cross-piece 31 is forwardly displaced from the column.

Two generally vertical arms 40, best viewed in FIGS. 1 and 2, have lower sections 41 which are bent forwardly and upwardly to engage through diametric holes 35, at the ends of tube 31. The ends of the arm sections 41 are held in place by pins 36.

Within the tube 31 is a cord 37 made of nylon or similar strong fibre which is wound around and between the interior portions of the arms 41 as shown more clearly in FIG. 8. As shown by the dotted lines, lengths of the cord cross between the respective arms 41 and pass through a clamp ring 38, one or more lengths *37a* also passing between the clamp ring 38 and the interior surface of the tube 31. A bolt 39 having a knob *39a* passes through the split ring 30 and engages the clamping ring 38 so that the cord length *37a* can be clamped between the ring and the interior surface of the tube 31. Parts of the cord 37 are clamped as shown in FIG. 7 to the arms 41, so that when the knob *39a* releases the cord, the arms can be adjusted in spacing. The ends of the arms 41 are caused to rotate by the cord 37 by equal and opposite amounts. This ensures that the patient is always centrally positioned. Pins *36a* prevent sideways displacement of the tube 31 relative to the split ring 30.

Returning to FIGS. 1 and 2, the arms 40 are seen to consist of lower sections 41 telescopically connected to upper sections 42 via clamp assemblies 50, which also serve as mountings for a buttock support 60 which consists of two separate sections 61,62 of fabric which are mutually attachable as shown in FIG. 2 e.g. by a Velcro (Trade Mark) fastening or in any other adjustable manner. One of the assemblies 50 is shown in more detail in FIGS. 9 and 10. Arm sections 41 and 42 telescopically interengage and are surrounded by a sleeve 51. This acts both as an anchor for the buttock support sections, each of which is stitched at one end around one of the sleeves 51, and as a means of interlocking the telescopically engaged arm sections 41,42. At each end, the sleeve is split as indicated at 52 and surrounded by a clamping ring 53,*53a*. Since the upper arm section 42 is narrower than the section 41, the upper section 42 requires packing 54 between it and the sleeve 51, shown in FIG. 10. The rings 53,*53a* are each clamped by a respective clamping lever 55,*55a* which operates through a cam nut 56,*56a*. Movement of the lever to the vertical in each case clamps the clamping ring which in turn clamps the end of the sleeve against the respective arm section 41,42, clamping the arm sections together.

When both clamping levers 55,*55a* are in a vertical, clamped position, a sleeve 57 may be slid along one of the levers to couple with the other lever, so that the lever assembly forms a continuous rod parallel to the arm 40. The buttock support sections may each be wound as many times as desired around the entire assembly and this prevents unwinding when tension is applied to the fastened support sections. The length of the buttock support can be adjusted in this way.

Figure 11:
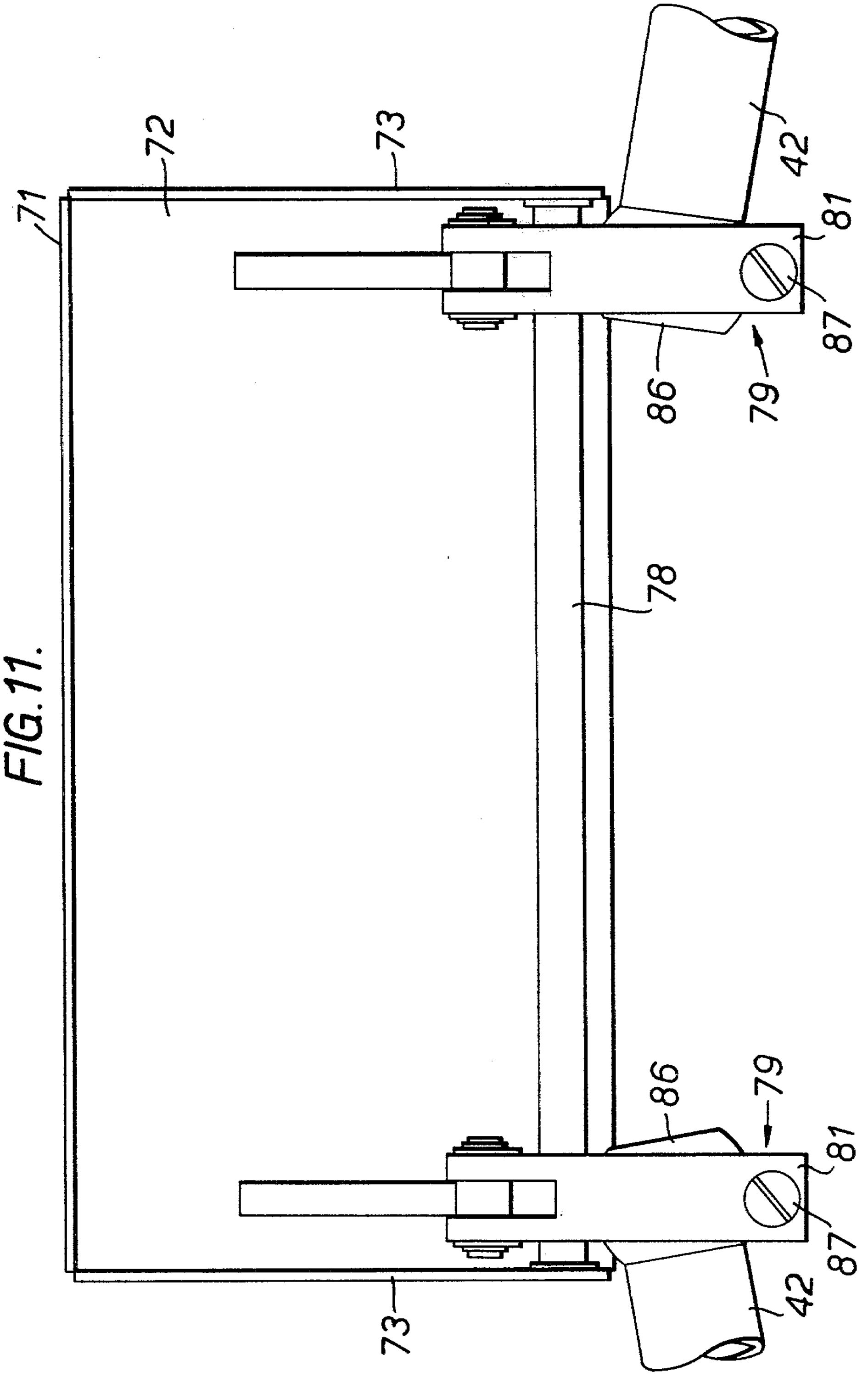
FIG. 11 is a reverse elevational view of the chest support showing the connection of the arms.
Figure 12:
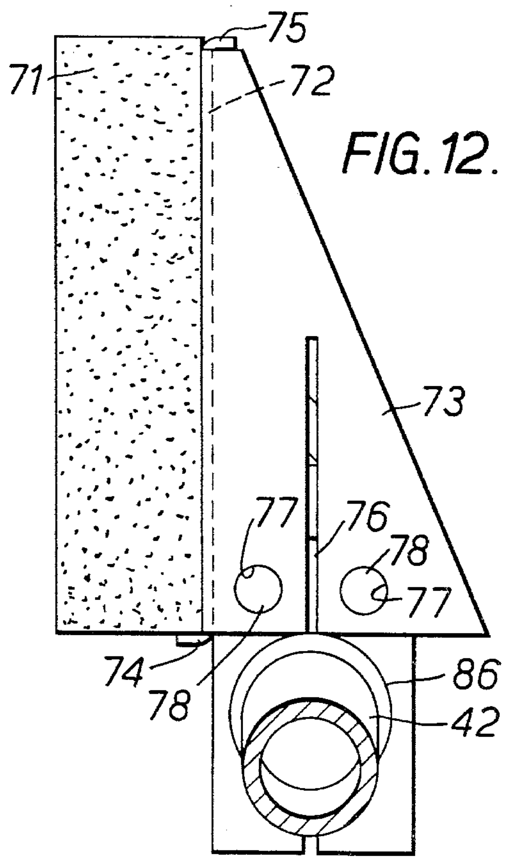
FIG. 12 is a side elevational view corresponding to FIG. 11.
Figure 13:
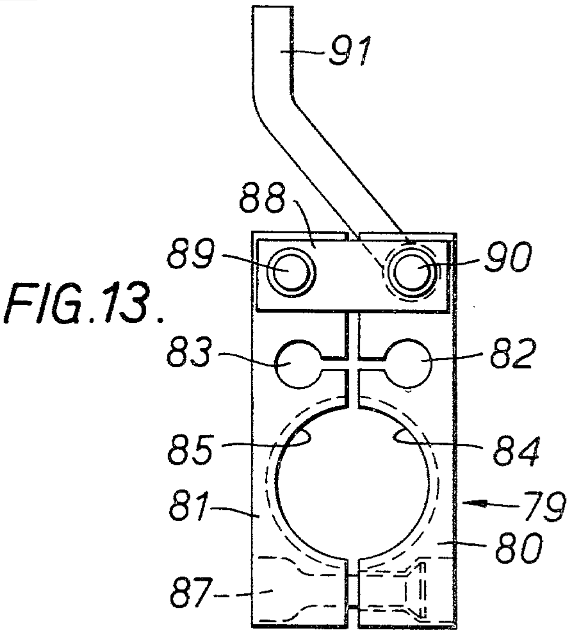
FIG. 13 is a view equivalent to FIG. 12 showing an arm clamp in more detail.

Returning to FIGS. 1 and 2, the upper arm sections 42 are each connected to a chest support 70, which is shown in more detail in FIGS. 11, 12 and 13. A block 71 of foam plastics (or rubber) material is adhered to a back plate 72, the ends of which are folded at right angles away from the block 71 to provide generally triangular flanges 73. A lower edge of the back plate is folded forwardly to form a flange 74 which provides some support for the block 71 and the upper end of the plate is bent backwards to provide a flange 75. Each of the flanges 73 is split as shown at 76 (FIG. 12) and on respective sides of the split near the base there are two bores 77 to accommodate two rods 78 which are rigidly attached to the flanges 73,73*a*.

Slidably mounted on the rods 78 are two clamp units 79 as shown in FIG. 13 each of which forms a mounting for one of the arm sections 42. Each clamp unit 79 is formed from two blocks 80,81 which are essentially similar. They are provided with respective splits bores 82,83 for the rod 78 and matching semi-circular concavely machines openings 84,85 which together form a mounting for a part-spherically machined hub 86 at the end of each arm 42. At their lower ends, the blocks 80,81 of the clamping units are held together by an adjustable bolt 87. At their upper ends they are held together by a pair of plates 88 which are held to block 81 by a pivot pin 89 and to the block 80 by a cam pin 90. A lever 91 is associated with the cam pin 90 of each unit 79 and enables rotation of the cam pin to pull the blocks 80,81 together or apart. This has the effect of clamping the spherical tube end 86 and simultaneously clamping the blocks 80,81 against the respective rods 78 via the slots in the wall of the bores 82,83. Therefore when each lever 91 is slackened there is freedom of motion of the clamping units 89 towards each other and apart along the rods 78 and also freedom of spherical pivoting of the arms 42 relative to the clamping units 79. In this way the clamp assembles the position of the chest or thorax support pad to be adjusted in relation to the arms 40 in three planes.

Figure 3:
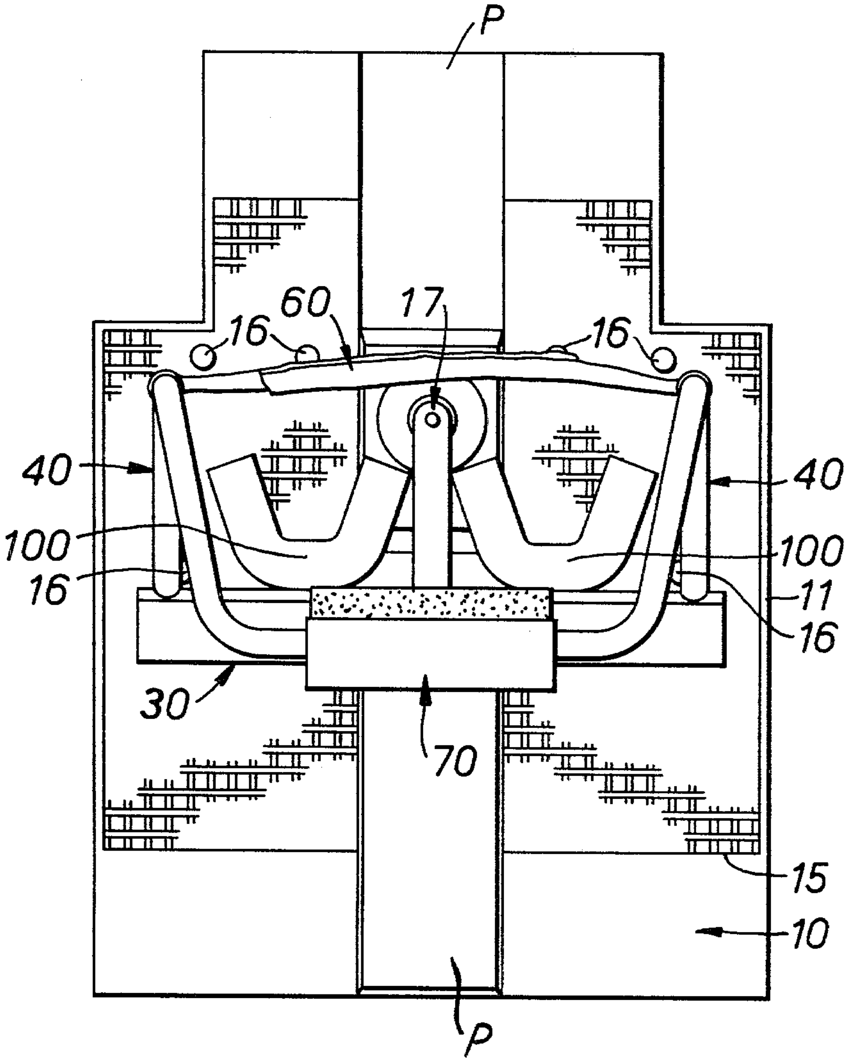
FIG. 3 is a top plan view of the platform of the frame.
Figure 15:
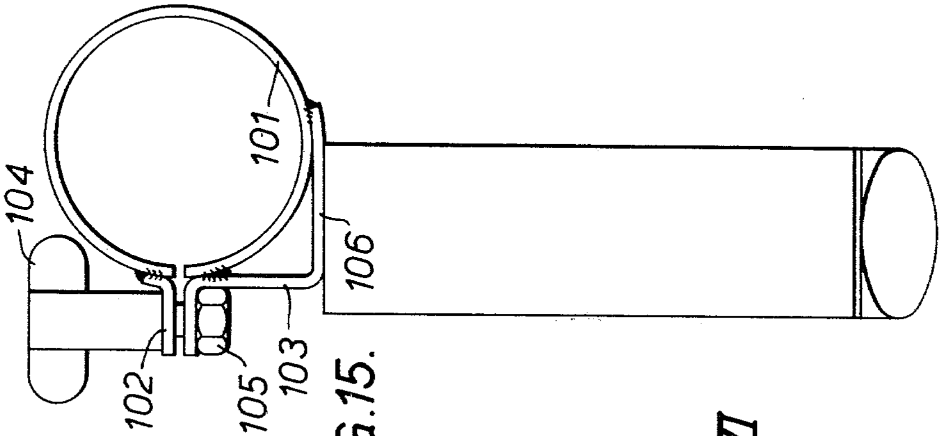
FIG. 15 is an end elevational view corresponding to FIG. 14.
Figure 16:
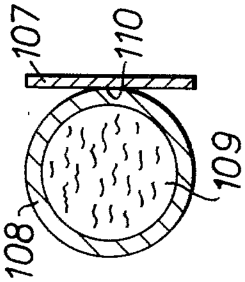
FIG. 16 is a section along XVI—XVI of FIG. 14.
Figure 14:
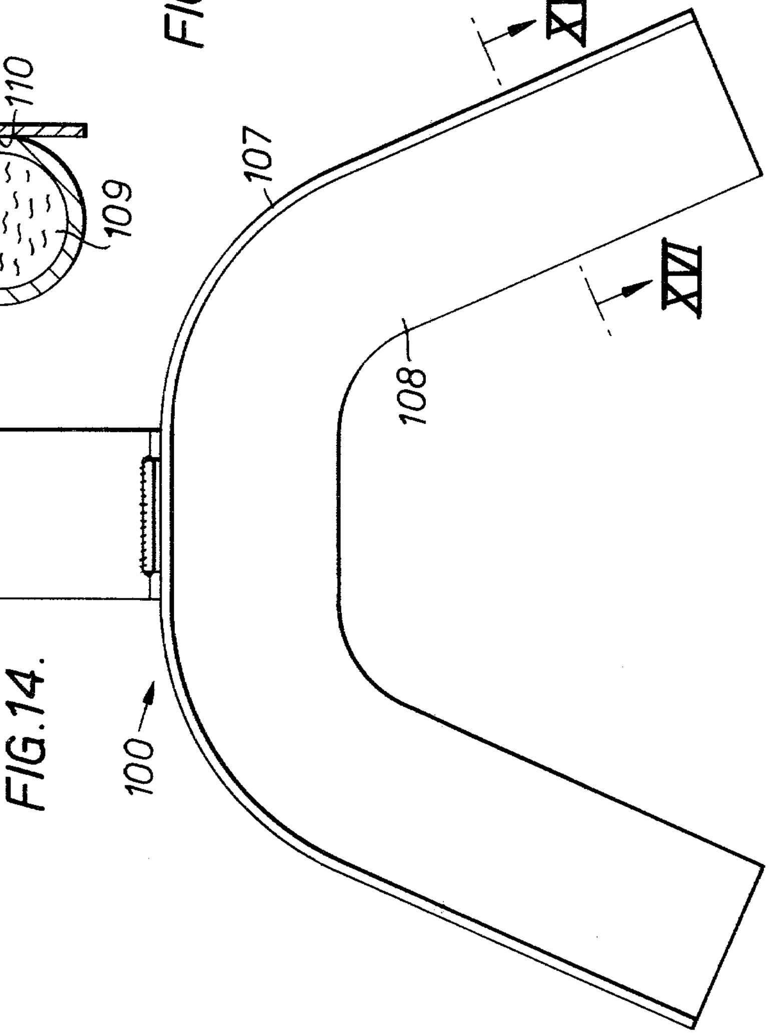
FIG. 14 is a top plan view of a knee rest.

Turning to FIG. 3, it will be seen that attached to the knee support 30 are two knee rests 100. These are shown in more detail in FIGS. 14, 15 and 16. Each knee rest 100 comprises a split ring 101 which passes over the tube 31 and has attached to it flanges 102,103 enabling the ring to be tightened by a wing nut 104 and bolt 105. The flange 105 is bent to form a bracket portion 106 which is welded to a strip 107 of steel or other bendable metal and which is bowed in plane as shown in FIG. 14 so as to fit around a knee. Bonded to the concave side of the strip 107 is a tube 108 of rubber or similar flexible and preferably elastic material. The tube 108 is sealed at its end and contains a fluid, preferably a viscous liquid such as a silicone or a cellulose gel 109.

The knee rest is designed to contact the knee on the patella tendon below the knee-cap (patella) where pressure may comfortably be taken. The gel within the tube and the elasticity of the tube combine to distribute the pressure evenly over the maximum contact area. Since the tube is bonded along a narrow line (110) there is some freedom for the tube to roll up and down relatively to the plate 107. This rolling motion allows relative vertical movement between the knee rest assembly and the knee, to be absorbed.

The mounting for the column 17 is more particularly described with reference to FIG. 17. The mounting is designed to allow the whole support frame to pivot to a limited degree relatively to the base. The movement is restricted to a maximum of $12\frac{1}{2}°$ from the vertical in any direction. The axis of movement is split into lateral (i.e. across the width of the base) and front/rear so that differing stiffnesses may be set in each plane. The stiffness between the axes will then be in proportion to the stiffness of the closest axis. To enable the two respective resilient means which cause the resistance to motion across the two axes mentioned, to be conveniently located, two separate articulations (articulated couplings) are provided each of which convert the pivotal movement of the column in one of the two planes to horizontal piston movements, which are conveniently arranged for front/rear movement and arranged parallel. Each of the piston movements, as will become apparent is restrained by an adjustable resilient restraint which is conveniently provided by a series of compressible blocks of elastomeric material such as rubber.

Figure 17:
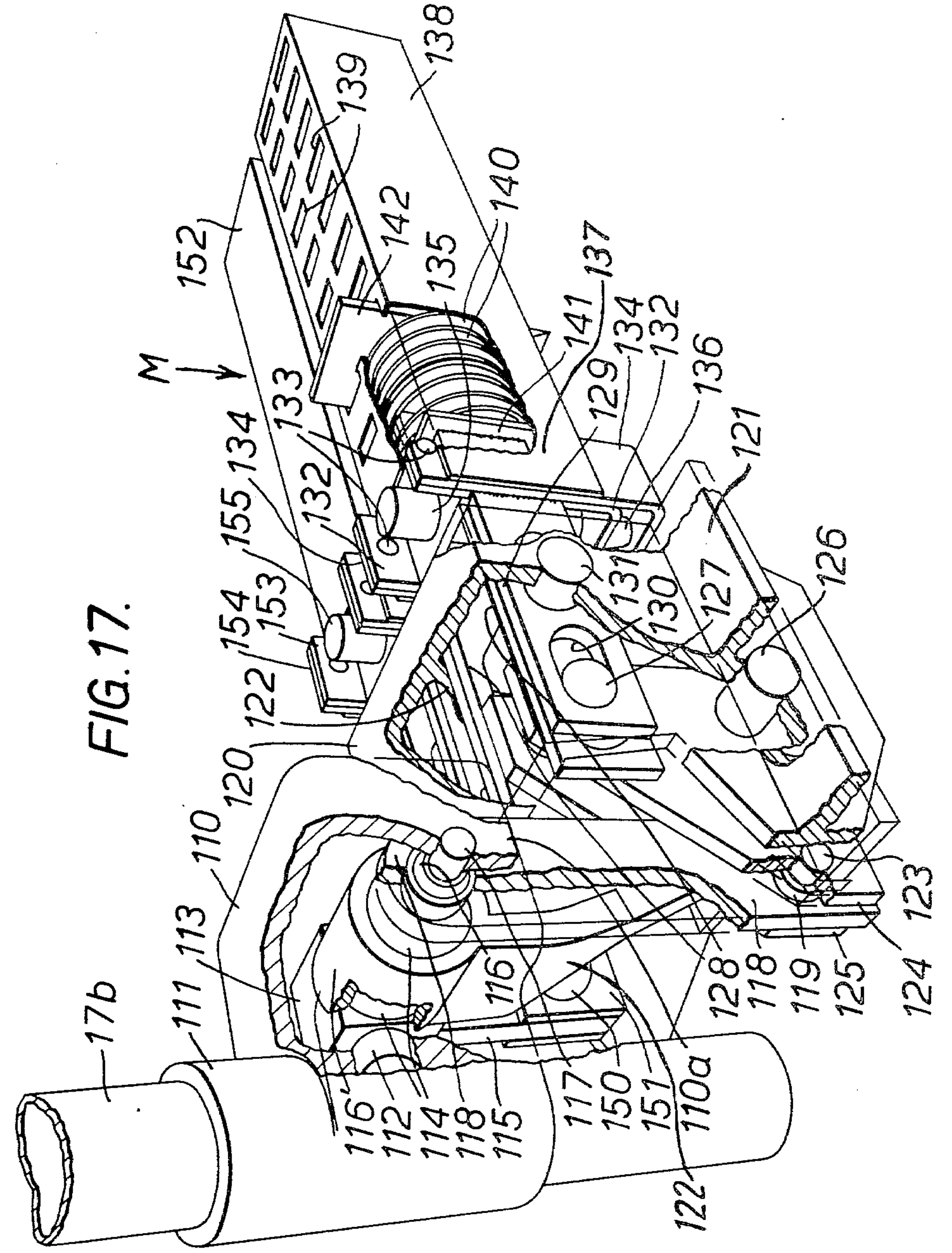
FIG. 17 is a perspective cut-away view of the column articulation and restraining means.

Turning to FIG. 17, the lower section 17*b* of the column 17 passes through a sleeve portion 111 of a first casting 110 which, apart from the sleeve 111, is generally of open bottomed rectangular shape. A stub shaft 112 extends forwardly within a bore in sleeve portion 111, rotatably through a block 113 and through a further bearing bore in the casting 110 (not shown). The block 113 is attached to a spigot 114 and to a drop arm 115. The spigot 114 rotatably passes through a boss 116′ which is part of a second casting 120. The casting 120 is generally formed as a rectangular box with lateral flanges 121 which are boltable to the platform 10 and a central dividing web 122 which essentially divides the two articulations.

Therefore the casting 110 is able to rotate to a limited degree on the axis formed by shaft 112 which in turn may rotate to a limited degree on the axis divided by spigot 114. The movements about the axis of shaft 12 cause the end of the casting 110, shown at 110*a* to rise and fall. Portion 110*a* contains a bore mounting a spherical bearing 116 the ball portion of which is mounted via a rigidly attached spigot 117. A vertical coupling 118 of rectangular section couples with spherical bearing 116 at one end and a further spherical bearing 119 at its lower end. A bolt 123 passes through the bearing 119 and is pivotally coupled to two triangular levers 124,125 on respective sides of the limb 118.

As casting portion 110*a* rises and falls, the triangular levers 124,125 are caused to rotate about a shaft 126 which passes through the central right angled portion of each triangular lever and is mounted at its ends in the side and web walls of casting 120. The rotation of the levers 124,125 about shaft 126 is converted to an essentially horizontal, oscillatory movement at the upper corner of the triangular levers where there is fixed a shaft 127.

The free ends of shaft 127 pass through two pairs of bars, an inner pair being marked 128 and an outer pair marked 129. Each of the bars 128, 129 has a slot 130 to receive the shaft 127. The slots are so arranged that those of the pair 128 bear against the forward end (away from the column 17) of the shaft 127 in operation and the slots of the pair 129 bear against the opposite, rearward circumferential face of the shaft 127. Thus when the column 17 is moved in one lateral direction it pushes against bars 128 but passes freely within the slots of bars 129 and, conversely, when it moves in the opposite lateral direction it pulls the bars 128 but passes freely within the slots of bars 129.

A shaft 131 passes through a second slot in each of the bars 128,129, which is forwardly spaced from the slots 130. The arrangement is such that the shaft 131 and the shaft 127 are at the same ends of the two slots in each bar 128,129. The shaft 131 is mounted within the side and web walls of casting 120.

The ends of the pair of bars 129 are welded to an inner U-shaped strip 132. This is pivotally attached by means of pivot pins 133 to an outer U-shaped strip 134. A vertical pin 135 passes through holes in the inner U-shaped strip 132 and is provided with a tapered end 136 which passes through a hole in the outer U-shaped strip 134. The pin 135 provides a means of adjustably locking together the lower ends of the U-shaped strips 132,134 so that in conjunction with pivot pins 133 these components may be strongly held together. Attached to the outside of outer U-shaped strip 134 are flanges 137 projecting from the rearward ends of a square tube 138. The tube 138 is perforated through its upper and lower faces by pairs of rectangular holes 139.

Contained within tube 138 is a series of rubber compression springs 140 of circular or square section. Each spring 140 takes the form of a series of parallel steel plates to which are moulded and bonded rubber blocks.

The inner pair of bars 128 pass through the channel of inner U-shaped strip 132 and terminate at a plate 141 to which they are welded. The springs 140 bear against the plate 141 at the rearward end. A steel tongue 142 may be inserted through any of the pairs of rectangular slots 139 so as to separate the rubber springs 140 where inserted. In this way any number of springs may be brought into operation as desired. To facilitate the insertion and removal of tongue 142, a downward pressure may be applied to the end of tube 138 so that pin 135 may be lifted out of the holes and tube 138 may then be pivoted upwards so that any precompression of the springs 140 is removed.

When the shaft 127 pulls against bars 129, the tube 138 is pulled so that the tongue 142 bears against the springs 140, which in turn bear against the plate 141. The movement of the plate 141 is prohibited by bars 128 which in turn bear against the shaft 131.

Conversely when the shaft 127 pushes against the bars 128, the plate 141 compresses the springs 140 which bear against the tongue 142, which causes the tube 138 to pull on the bars 129 which movement is prohibited by the shaft 131.

Thus by adjustment of the number of springs 140 in tube 138 which are brought into operation, oscillatory movements of the column 17 are resisted in the lateral plane.

Movements of the column in the fore and aft direction, i.e. at right angles to those abovedescribed, are passed through the shaft 112 and block 113 to the drop arm 115. The arm 115 is linked by a shaft 150 to bars 151 which are therefore caused to oscillate in a horizontal plate generally parallel to the bars 128,129. Bars 151 have at their opposite ends a second shaft equivalent to shaft 127 and the resistance to movement of the column in this plane is exactly as already described with reference to movement in the other plane, the rubber springs (not shown) being housed within a square tube shown at 152. The inner U-shaped strip associated with square tube 152 is shown at 153, and the outer U-shaped at 154. The pin equivalent to pin 135 is indicated at 155. Slots equivalent to the slots 139 have been omitted from the drawing for the sake of clarity and likewise a tongue equivalent to tongue 142.

Thus adjustments made to springs within the square tube 152 prescribe the degree of stiffness for movements in the front/rear plane.

Figure 4:
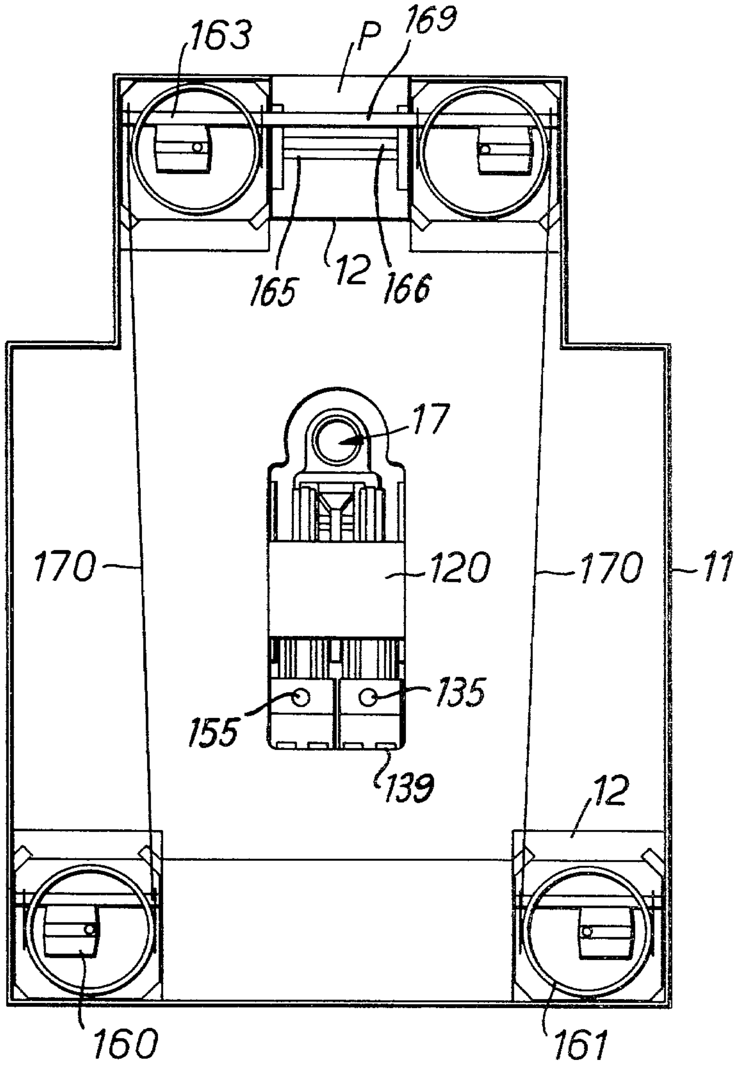
FIG. 4 is a bottom plan view of the platform.
Figure 18:
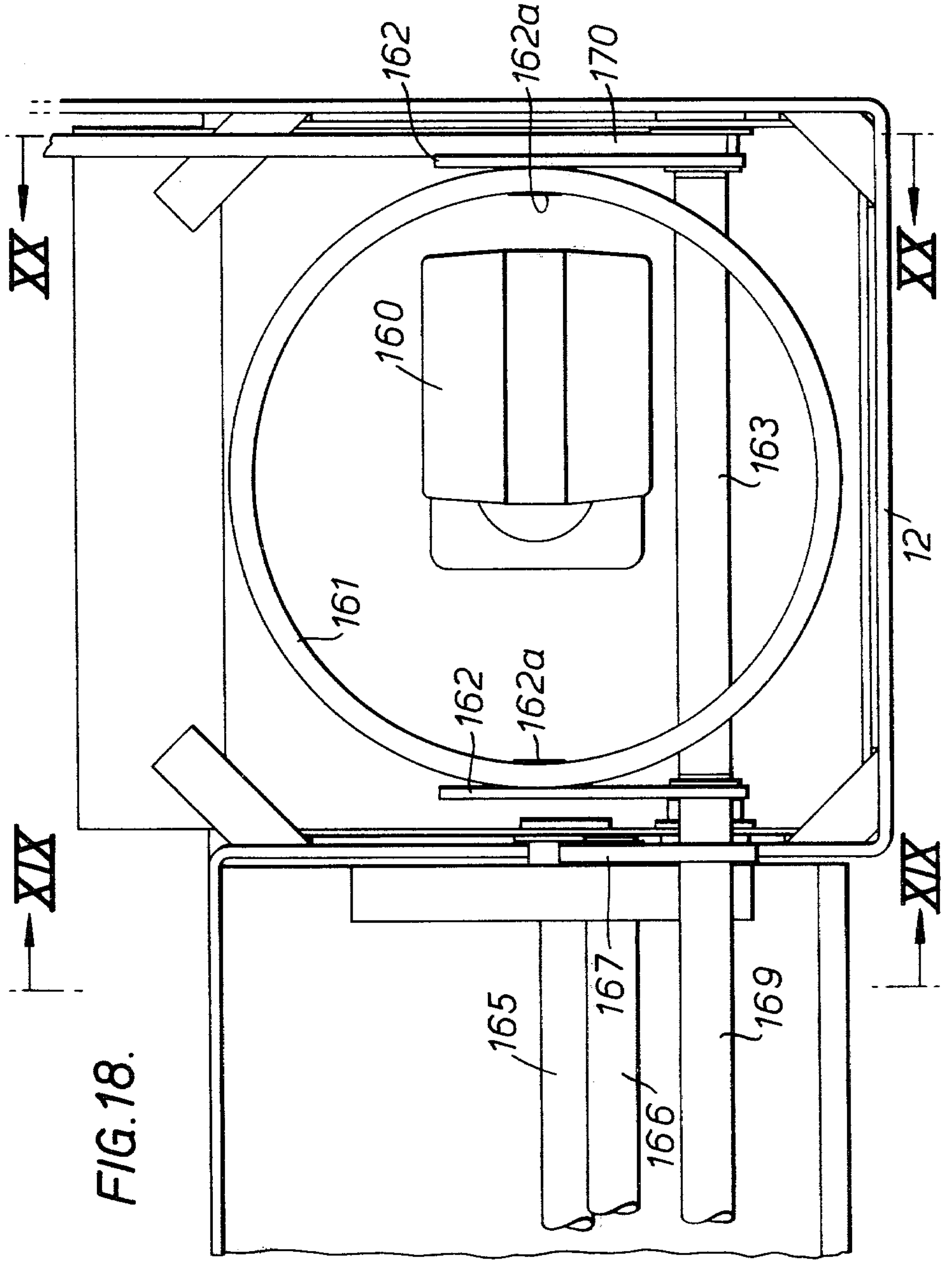
FIG. 18 is a bottom plan view of the platform enlarged to show one castor and its supports.
Figure 19:
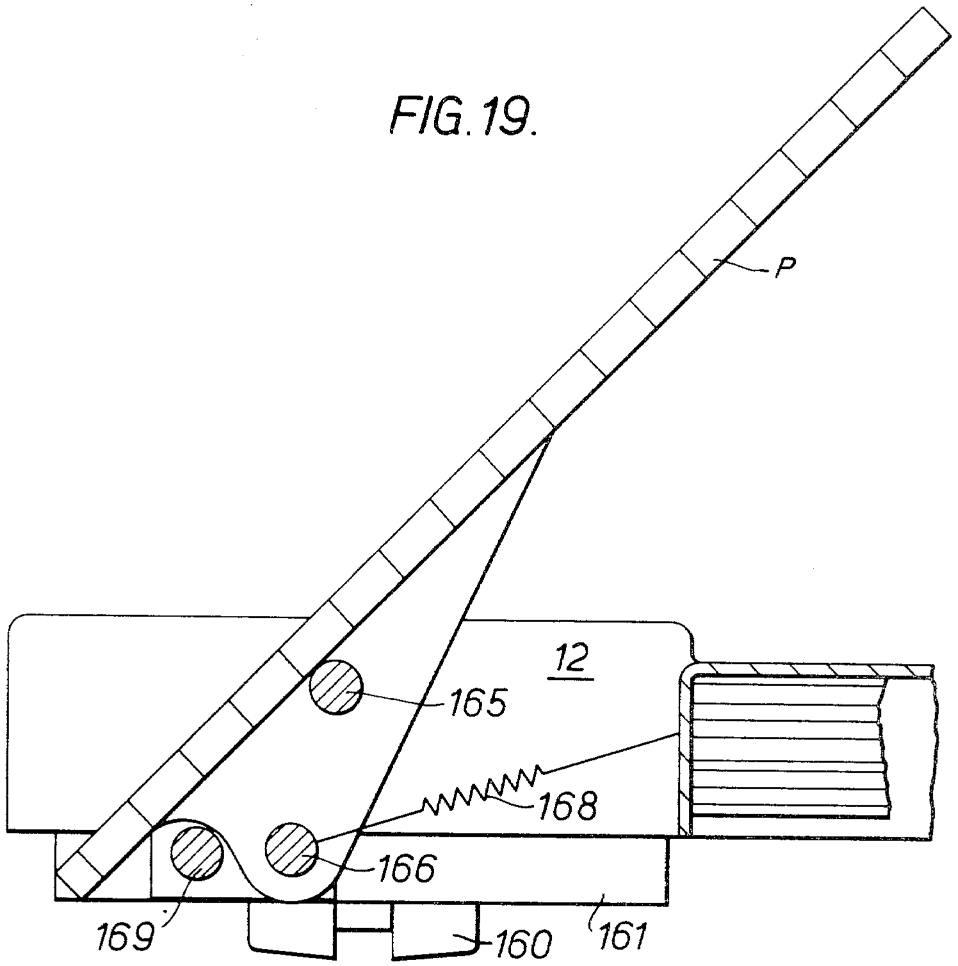
FIG. 19 is a section along XIX—XIX of FIG. 18.
Figure 20:
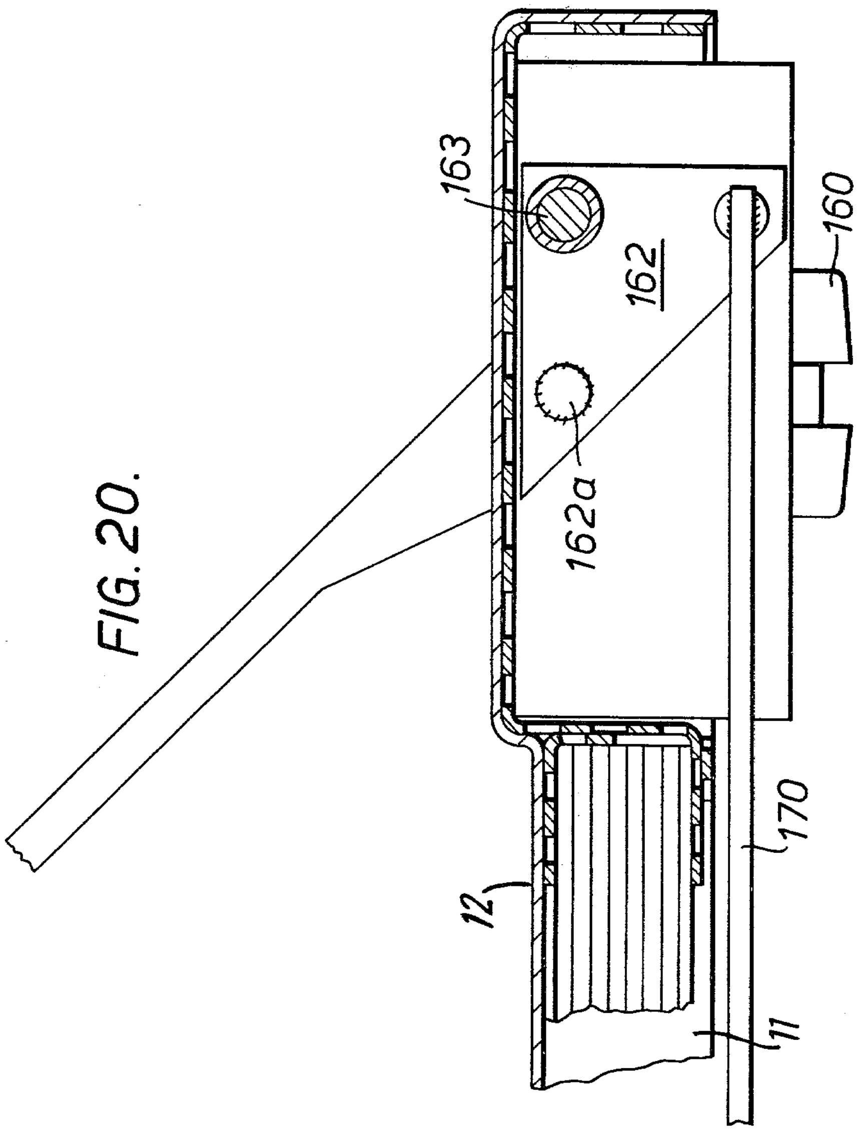
FIG. 20 is a section along XX—XX of FIG. 18.

The castor operating assembly is shown in FIGS. 18, 19 and 20, together with FIG. 4. The castors 160 are mounted to mounting frames 12 fixed to the base 11. Rings 161 are pivoted by pivots **162*a* diametrically to levers 162 coupled to a shaft 163. The shaft 163 is rotatably mounted to a frame 12 (FIG. 4) so that the ring 161 moves relatively to the platform base 11**.

A pedal P is attached to and pivotally mounted by a shaft 165 mounted to the frame 12. Also fixed to the pedal is a shaft 166, the ends of which are attached to links 167. A spring, diagrammatically shown at 168, is attached between shaft 166 and the frame 12. The links 167 are also attached to shaft 169. This is also attached to the lever 162 which is in turn attached to and pivoted on the shaft 163.

When the toe end of the pedal is pressed down, the shaft 166 causes the links 167 to move the shaft 169 which moves the two levers 162 about the shaft 163, forcing the ring 161 downwards. As the pedal reaches the horizontal position, the shaft 166 passes the top dead-centre position which is the straight line between shafts 165 and 169 and is locked in place by a toggle action. In this position, as shown in e.g. FIG. 1, the castor-surrounding rings 161 are in contact with the ground. Pressure on the heel end of the pedal has the reverse effect, raising the castor surrounding rings relative to the frame 12 and the castors.

The right-hand lever 162 in FIG. 18 is linked to link rod 170 which operates a similar mechanism at the opposite end of the platform. At the same end of the platform, the shaft 169 operates upon the other castor. In this way all the rings may be lifted off or lowered over the four castors.

In operation the patient is sat behind the frame with his feet on the grid and his knees near the knee rests. The height of the knee rest is then adjusted by adjusting the column. The distance between the arms 40 is then adjusted by measurement or estimation of the patient's hip width. The height of the buttock support is then estimated and adjusted.

The patient may now be held in a standing position and the buttock support sections fastened behind the buttocks. The chest or thorax pressure support pad may then be adjusted for height. The fore and aft position of the chest support is then adjusted so that the patient is supported vertically. The angle of the chest support is then adjusted so that the foam pad fits the thorax.

The buttock support sections can then be readjusted for height and tightness as necessary. The knee rests can then be adjusted laterally. The feet positions can be readjusted if necessary and the studs placed in position and then the stiffness of the springs 140 should be adjusted to suit the size, weight and motor activity of the patient.

When it is required to move the frame with or without the occupant, the foot pedal is operated to raise the castor rings.

The patient can obtain some therapeutic exercise by a pivotal movement of the frame about its resilient support and if necessary of desired some locking means may be provided for restricting or excluding such pivotal movement. The patient can be moved from one place to another by operating the pedal P to engage the castors whereupon the whole platform and patient can be pushed. It will be appreciated that in the course of any pivotal movement of the column 17, the frame will pivot as a whole without any relative movement of the two arms, whereas the knee support will be movable to accommodate small height differences between the knees.

The various components of the frame can be made of any suitable material. Thus the column sections are preferably of steel tubing and the platform of moulded reinforced plastics or metal pressings or castings or wood. The arms may be of tubular steel or aluminium or alloys thereof and the pads are foamed rubber or plastics material such as resilient polyurethane or any other suitable material. The buttock support may be of canvas or woven synthetic material.

The reverse side of the chest support 70, the column mounting components and the cross-piece 31 are shown in FIG. 1 protected by moulded plastics covers.

I claim:

1. A standing support frame for handicapped persons comprising a platform, a column mounted upright on the platform so as to be pivotable to a limited degree in all directions from a mean position, means for resiliently urging the column to said mean position, a pair of upright horizontally spaced support arms, a knee support including a cross-piece mounted to the column, said arms being joined at their lower ends to said cross-piece and at their upper ends to a chest support, and a buttock support extending between said arms at an appropriate position, wherein said arms extend rearwardly from said knee support, upwardly at a rearward spacing from the column and forwardly above said buttock support to said chest support.

2. A standing frame according to claim 1 wherein said cross-piece is forward of said column and said arms extend therefrom downwardly and then upwardly, an upper part of said column extending forwardly to join said knee support.

3. A standing frame according to claim 1 or claim 2 wherein each arm includes a clampable telescopic joint.

4. A standing frame according to claim 1 or claim 2 wherein the column is adjustable in height.

5. A standing frame according to claim 1 or claim 2 wherein the spacing of the arms at the chest support is adjustable.

6. A standing frame according to claim 1 or claim 2 wherein the platform has castors fixed thereto, and is liftable off the ground by downward displacement of movable supports.

7. A standing frame according to claim 1 or claim 2 wherein the knee support includes a pair of knee rests each comprising a flexible tube section attached to a shaped former and filled with a fluid or gel.

8. A standing frame according to claim 1 wherein said cross-piece mounts the ends of the arms with provision for their pivotal movement to allow adjustment of their spacing.

9. A standing frame according to claim 8, wherein means are provided for ensuring that during adjustment of the spacing of the arms the arms are moved by equal and opposite amounts.

10. A standing frame according to claim 1 wherein the resilient means includes respective lateral and front-/rear articulations each having a respective adjustable resilient restraint.

11. A standing frame according to claim 10, wherein the resilient restraints include a series of compressible blocks of elastomeric material, the number of blocks in operation being selectable.

* * * * *